United States Patent [19]
Li et al.

[11] Patent Number: 5,418,058
[45] Date of Patent: May 23, 1995

[54] CHEMICAL MICROSENSORS

[75] Inventors: DeQuan Li; Basil I. Swanson, both of Los Alamos, N. Mex.

[73] Assignee: The Regents of the University of California, Oakland, Calif.

[21] Appl. No.: 132,391

[22] Filed: Oct. 4, 1993

[51] Int. Cl.6 .................................................. B32B 9/00
[52] U.S. Cl. ..................................... 428/327; 428/324; 428/339; 310/313 B
[58] Field of Search .................... 310/313 B; 428/324, 428/327, 339

[56] References Cited

U.S. PATENT DOCUMENTS

| | | | |
|---|---|---|---|
| 4,056,803 | 11/1977 | White et al. | 340/15 |
| 4,367,072 | 1/1983 | Vogtle et al. | 436/501 |
| 4,860,573 | 8/1989 | Barendz et al. | 73/23 |
| 4,895,017 | 1/1990 | Pyke et al. | 73/23 |
| 5,006,749 | 4/1991 | White | 310/323 |
| 5,015,843 | 5/1991 | Seitz et al. | 250/227.21 |
| 5,063,164 | 11/1991 | Goldstein | 436/169 |
| 5,129,262 | 7/1992 | White et al. | 73/599 |
| 5,130,257 | 7/1992 | Baer et al. | 436/151 |
| 5,151,110 | 9/1992 | Bein et al. | 55/75 |
| 5,189,914 | 3/1993 | White et al. | 73/599 |
| 5,190,663 | 3/1993 | Fetzer | 210/674 |
| 5,200,517 | 4/1993 | Uemasu et al. | 536/103 |
| 5,212,988 | 5/1993 | White et al. | 73/599 |
| 5,243,539 | 9/1993 | Holt et al. | 364/500 |

Primary Examiner—Patrick J. Ryan
Assistant Examiner—Kam F. Lee
Attorney, Agent, or Firm—Bruce H. Cottrell; William A. Eklund

[57] ABSTRACT

An article of manufacture is provided including a substrate having an oxide surface layer and a selective thin film of a cyclodextrin derivative chemically bound upon said substrate, said film is adapted for the inclusion of a selected organic compound therewith. Such an article can be either a chemical sensor capable of detecting a resultant mass change from inclusion of the selected organic compound or a chemical separator capable of reversibly selectively separating a selected organic compound.

12 Claims, 4 Drawing Sheets

CHEMICAL MICROSENSORS

FIELD OF THE INVENTION

The present invention relates to devices including a layer of a cyclodextrin for use in the field of chemical microsensors and to the detection of trace amounts of selected organic compounds or for use in the field of chemical separations. This invention is the result of a contract with the Department of Energy (Contract No. W-7405-ENG-36).

BACKGROUND OF THE INVENTION

Ever increasing concerns over pollutants within the environment, require improved monitoring and/or analysis for the detection of certain chemical species, e.g., organic compounds such as benzene. While analytical techniques are available to detect the presence of many substances down to levels as low as parts per billion or less, such analytical techniques generally require collecting a sample in the field, taking the sample to a laboratory, and analyzing the sample by, e.g., gas chromatography or mass spectroscopy. Such analysis requires sophisticated equipment that generally requires up to several days to obtain final results and such analysis is not generally suited to use in the field. Thus, present anayltical techniques fail to provide any real time information about the presence of pollutants or contaminants.

In an effort to overcome the limitations of present anaytlical techniques, much research has been directed to developing chemical sensors that can give more rapid feedback information. One example of such a chemical sensor is found in U.S. Pat. No. 5,151,110 wherein a sensor includes a piezoelectric substrate, preferably contained within a surface acoustic wave (SAW) device or a quartz crystal microbalance (QCM) device, and a coating, such as zeolite crystals in an inorganic silica matrix, applied to the substrate to selectively sorb chemical entities of a size less than a predetermined magnitude. While such a chemical sensor is useful, it is limited to materials that physically fit within the particular pore sizes of the zeolite crystals. Additionally, as the selective layer including the zeolite crystals and a polymeric binder material are coated onto the substrate by conventional coating techniques such as dip-coating, spraying, spin-coating and the like, the selective layer is subject to durability problems such as separation from the substrate due to poor adhesion.

U.S. Pat. No. 4,860,573 desribes a composite substrate intended for an apparatus for quantitative detection of, e.g., an organic component present in a gas or liquid. Cyclodextrin is described as one material for incorporation as an active site material into the composite substrate. However, there is no teaching or suggestion of multilayers of the active site material, nor is there any teaching or suggestion of using cyclodextrin derivatives or of forming oriented cycxlodextrin derivative structures by the controlled assembly of such materials.

It is an object of the present invention to provide a chemical sensor including a cyclodextrin derivative and a method of detecting chemical pollutants or contaminants, preferably in an on-site, real time process.

It is a further object of the invention to provide a chemical sensor, including a cyclodextrin derivative, having sensitivity to detect low levels of selected chemical pollutants or contaminants.

It is a still further object of the invention to provide a reversible chemical sensor including a cyclodextrin derivative.

Yet another object of the invention is to provide a chemical separator including a cyclodextrin derivative for reversibly separating selected chemical species.

SUMMARY OF THE INVENTION

To achieve the foregoing and other objects, and in accordance with the purposes of the present invention, as embodied and broadly described herein, the present invention provides an article of manufacture including a substrate having an oxide surface layer and a selective thin film of a cyclodextrin derivative chemically bound upon said substrate, said thin film adapted for the inclusion of a selected organic compound therewith. Such an article can be either a chemical sensor capable of detecting a change, e.g., a resultant mass change, from inclusion of the selected organic compound or a chemical separator capable of reversibly separating a selected organic compound.

The present invention further provides a method of detecting trace amounts of selected organic species within a gaseous or liquid medium by placing a selective chemical sensor into an environment, the sensor including a substrate having an oxide surface layer thereon and a selective thin film of a cyclodextrin derivative chemically bound upon the substrate, the film adapted for the inclusion of a selected organic compound therewith, for a sufficient time wherein selected organic species can form inclusion complexes with the cyclodextrin derivative, measuring a change resulting from formation of the inclusion complexes with the cyclodextrin derivative, and, correlating the measured change with a quantitative or qualitative output relating to the selected organic species.

DETAILED DESCRIPTION

The present invention is concerned with an article of manufacture, e.g., a device including a substrate with a layer of a cyclodextrin derivative thereon, such device useful as a chemical sensor and for detecting selected chemical species with such a chemical sensor, or useful as a chemical separator for reversibly separating selected chemical species.

The selective thin film or coating upon the substrate is preferably a size selective host material and can generally be selected from among, e.g., cyclodextrins. Each of the selective host materials should have a suitable opening or cavity wherein selective capture of inclusion of target organic compounds can occur.

The selective thin film can generally include a single layer of the cyclodextrin-derivative material or can include multiple layers of the cyclodextrin-derivative material. Multiple layers can be preferred to enhance sensitivity of the selective thin film by providing additional inclusion sites. In multiple layers, a second layer of the cyclodextrin-derivative material can be chemically bound upon bonding sites in the first layer of the cyclodextrin-derivative material. There is generally no limit to the number of layers that can be employed although usually the number of layers will be from about 1 to about 100.

Generally, the thin films are from about 2 nanometers (nm) to about 1 micron in thickness. In one embodiment, a second layer of a cyclodextrin derivative may be spin cast upon an initial layer of a cyclodextrin derivative deposited in a self assembly technique. When such a spin casting approach is used, thicker layers of the cyclodextrin derivative may be formed with film thicknessess from about 0.1 microns to about 5 microns.

Total film loading by weight of the selective thin film of the cyclodextrin-derivative material upon the substrate is important in providing adequate sensitivity to a chemical sensor. By using multiple layers, the total film loading can be increased and such larger loadings may be desired for some applications.

The present articles including the cyclodextrin-derivative material are useful for inclusion of selected organic compounds such as aromatic compounds, e.g., benzene, toluene, xylene and the like, polyaromatic compounds including compounds with fused ring structures containing between about two and ten rings, some or all of which are benzene rings, e.g., naphthalenes, indenes, anthracenes, phenanthrenes, fluorenes, acenaphthenes, benzanthracenes, perylenes, tetracenes, pyrenes, benzopyrenes, benzoperylenes, and the like, oxygen-containing organic compounds, e.g., methanol, acetone, dimethyl sulfoxide, dimethyl formamide, tetrahydrofuran and the like, and halogenated, e.g., brominated or chlorinated, hydrocarbons, e.g., chloroform, carbon tetrachloride, methylene chloride, trichloroethane, tetrachloroethene, dichloroethylene, trichloroethylene, and the like. $\alpha$-cyclodextrin is generally better suited for inclusion of smaller hydrocarbons, while $\beta$-cyclodextrin is generally better suited for inclusion of larger hydrocarbons, e.g., fused ring compounds such as naphthalenes.

Suitable cyclodextrin-derivative materials can be formed from materials including $\alpha$-cyclodextrin, $\beta$-cyclodextrin, $\gamma$-cyclodextrin or modified $\alpha$-cyclodextrins, $\beta$-cyclodextrins, or $\gamma$-cyclodextrins, preferably modified $\alpha$-cyclodextrins, $\beta$-cyclodextrins, or $\gamma$-cyclodextrins. Cyclodextrins are linked D-glucopyranose units with $\alpha$-cyclodextrin, $\beta$-cyclodextrin, $\gamma$-cyclodextrin being composed of 6, 7, or 8 units, respectively, the units linked into a circular arrangement. Accordingly, the internal diameter of each of $\alpha$-cyclodextrin, $\beta$-cyclodextrin, $\gamma$-cyclodextrin varies from the others. $\alpha$-cyclodextrin has a cavity size or internal diameter of about 4.7 to 5.2 Angstroms (Å), $\beta$-cyclodextrin has an internal diameter of about 6.0 to 6.5 Å, and $\gamma$-cyclodextrin has an internal diameter of about 7.5 to 8.5 Å.

The term "cyclodextrin derivative" refers to a cyclodextrin modified by the addition of other functional groups, e.g., a cyclodextrin wherein a hydrogen atom of one or more primary or secondary hydroxyl groups therein has been substituted by, e.g., a carboxyl group, a carboxyl alkyl group, a carboxylaryl group, an alkyl group, e.g., either a lower alkyl such as a $C_1$ to $C_4$ group or a longer chain aliphatic containing from about 8 to about 22 carbons, a hydroxyalkyl group, a sulfonic group, or an alkylenesulfonic group and the like. Modification of a cyclodextrin can alter the length and size of the internal cavity or alter the chemical compatibility or binding properties of the particular cyclodextrin derivative with a target chemical compound.

One manner of tailoring properties of a resultant article including multilayers of cyclodextrin derivatives may be to functionalize only the final outer layer of cyclodextrin, e.g., the last layer of cyclodextrin derivative may include a functional group selected so as to limit the potential of certain chemical species, e.g., water or chlorinated compounds to penetrate into the multilayer structure. Another manner of tailoring the properties may be to use a cyclodextrin derivative including as a functional group, e.g., a hydroxyalkyl group so that each cyclodextrin derivative layer includes a hydrophobic linkage, i.e., the alkyl group, and then using a different cyclodextrin derivative as the final layer, e.g., the final cyclodextrin derivative having a functional group such as an aliphatic group containing from about 8 to about 22 carbons thereby excluding polar molecules such as nitrobenzene but allowing lower alkanes into the structure for detection or separation. Yet another benefit of tailoring the cyclodextrin derivative functionality may be to alter the retention times of the particular species.

Figure 4:
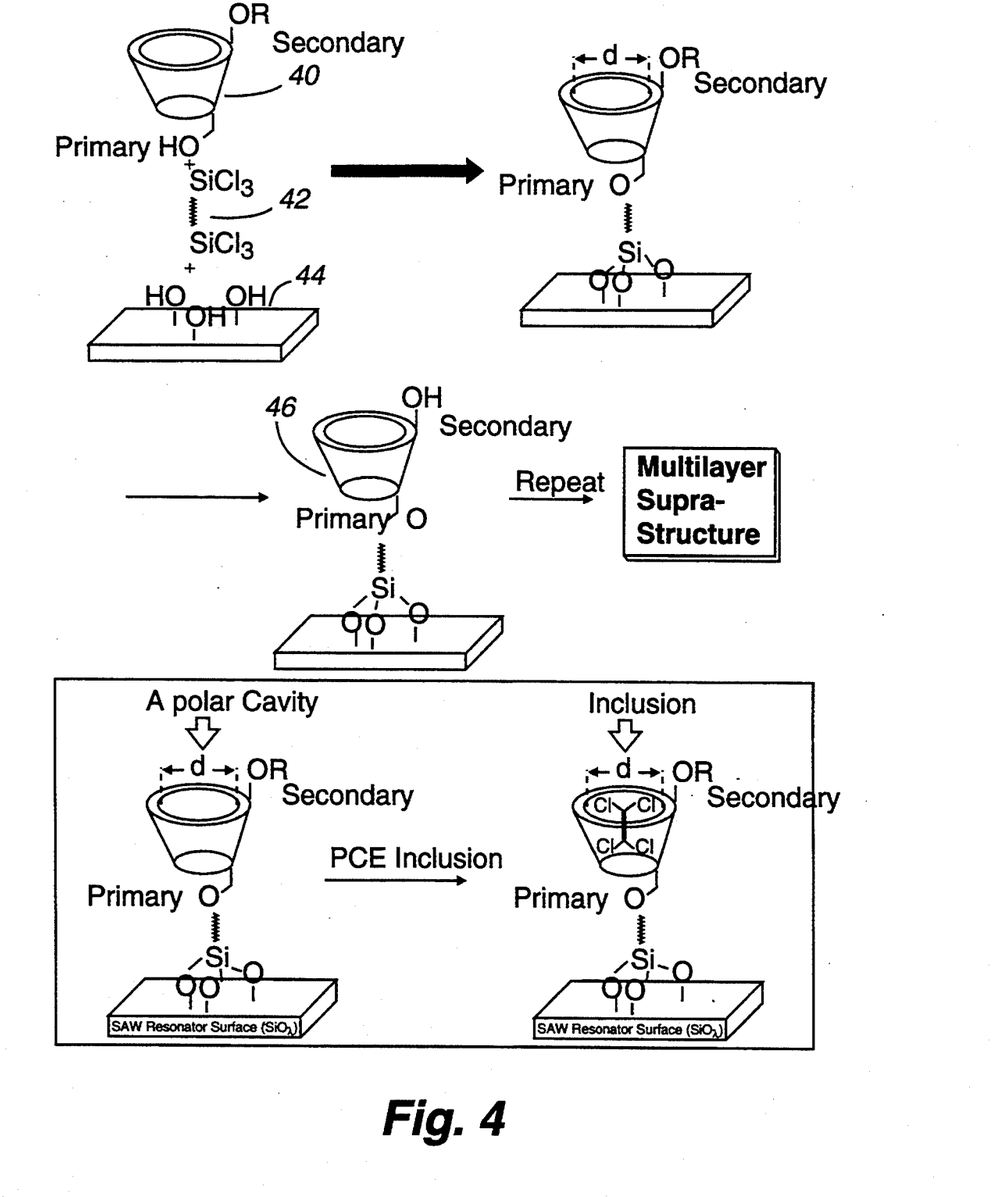
FIG. 4 illustrates a self-assembly scheme in accordance with the present invention.

FIG. 4 shows a syntheic scheme or self-assembly scheme useful in practicing the present invention. In a cyclodextrin derivative 40, a secondary hydroxyl group has been reacted to convert the hydroxyl group to an ester group (OR). R in such an ester group can include a carbonyl group such as $R_1C(=O)$— with $R_1$ being, e.g., hydrogen, an alkyl group, preferably a $C_1$ to $C_4$ alkyl group or substituted $C_1$ to $C_4$ alkyl group, or an aryl group, preferably a phenyl or substituted phenyl. R can also be an alkyl group, preferably a $C_1$ to $C_4$ alkyl group or substituted $C_1$ to $C_4$ alkyl group, an aryl group, preferably a phenyl or substituted phenyl, or a sulfonic group and the like. Suitable groups for R can include: carboxyl groups wherein $R_1$ is methyl, ethyl, propyl, butyl, hydroxyethyl, hydroxypropyl, benzyl, and the like; alkyl groups such as methyl, ethyl, propyl, butyl, hydroxyethyl, hydroxypropyl, benzyl, and the like; or, aryl groups such as phenyl and the like. Derivative 40 can be linked in step (b) through silane linker 42 after silane linker 42 is initially reacted in step (a) to the oxide surface of substrate 44. Orientation of the cyclodextrin cavity as shown can thus be accomplished. Reaction in step (c) with potassium hydroxide and methanol can restore a secondary hydroxyl functionality as shown at 46 and steps (a), (b), and (c) can be repeated to build up a multilayer structure with oriented cyclodextrin functionality.

For example, monolayers of both asymmmetric $\alpha$- and $\beta$-cyclodextrin benzoate derivatives on a oxide layer can be successfully functionalized through covalent bonds via a linker such as a bis(trichlorosilyl)alkane. The benzoate group can be hydrolyzed off by treatment with an aqueous base, e.g., aqueous potassium hydroxide with six equivalents of methanol yielding resultant hydroxyl groups. In this manner, surface properties of the cyclodextrin derivative such as relative hydrophilicity or hydrophobicity can be tailored. Such tailoring of the properties can change the selectivity of the cyclodextrin derivative to various target organic compounds.

Multilayers of the cyclodextrin derivative can be built up by attaching a linker to surface hydroxyl groups, whether original cyclodextrin hydroxyl groups or subsequently generated hydroxyl groups. Such a linker can be a silane such as 1,6-bis(trichlorosilyl)hexane followed by linking of additional cyclodextrin molecules through their primary hydroxyl groups. The construction of such multilayered cyclodextrin derivatives can be in a fashion refered to as self assembly and can be accomplished by first anchoring α-cyclodextrindodeca(2,3)benzoate to a silane linker, e.g., 1,6-bis(trichlorosilyl)hexane, and then removing the benzoate blocking groups via hydrolysis to reform the surface or secondary hydroxyl groups. These surface or secondary hydroxyl groups can then be reacted with another silane linker thereby forming a terminal surface functionality allowing the attachment of additional cyclodextrin units through their primary hydroxyl groups.

In addition to covalent bonding to the oxide surface, such a step by step supramolecular self assembly technique offers molecular level manipulation of the nanostructure of the resultant material, e.g., in the orientation of the cyclodextrin derivatives. As both the α- and β-cyclodextrin secondary hydroxyl groups can be blocked by reaction to form benzoate groups, the building blocks of the cyclodextrin derivatives can easily be assemblyed with a molecular orientation ensuring that the cyclodextrin "bucket" faces outward from the initial oxide surface of the substrate thereby enhancing the response time in the formation of the inclusion complexes. Other functionalities attached to the secondary hydroxyl groups of the cyclodextrin may control access to the "bucket" or cavity of the cyclodextrin.

Cyclodextrins are commercially available, e.g., from Sigma Chemical Co., St. Louis, Mo.

The substrates in the presently described invention are generally materials such as quartz, silicon, zinc oxide, zirconium oxide, tin oxide, indium-tin oxide, titanium oxide and lithium niobate. The substrates can be a part within a device such as a SAW device, a Lamb wave device, or an optical transducer, e.g., a waveguide device such as a Mach-Zender interferometer. The substrate can also be in the form of, e.g., beads for use as a separation media.

The process of forming articles or devices including substrate with an oxide surface layer and the selective thin film of a cyclodextrin-derivative material generally includes use of a silane linking agent between the oxide surface layer of the substrate and the cyclodextrin-derivative material. Among useful silane linking agents can be included 1,6-bis(trichlorosilyl)hexane, 1,8-bis(trichlorosilyl)octane, 1,6-bis(chlorodimethylsilyl)hexane, 1,8-bis(chlorodimethylsilyl)octane, 1,3-dichlorotetramethyldisiloxane, 1,5-dichlorohexamethyltrisiloxane, 1,7-dichlorooctamethyltetrasiloxane, 1,4-dimethyl-1,1,4,4-tetrachloro-1,2-disilethylene, hexachlorodisilane, 1,1,4,4-tetramethyl-1,4-dichloro-disilethylene, and para(chloromethyl)phenyl trichlorosilane.

The silane linking agent can be reacted initially with the oxide surface layer of the substrate and then subsequently with the cyclodextrin-derivative material or may be initially reacted with the cyclodextrin-derivative material and then subsequently with the oxide surface layer of the substrate. After formation of the initial layer, a subsequent layer of the cyclodextrin-derivative material can be linked through additional silane linking agents linked to, e.g., a hydroxyl functionality of the first cyclodextrin-derivative material layer. Alternatively, a subsequent layer of the cyclodextrin-derivative material can be linked directly to, e.g., a hydroxyl functionality of the first cyclodextrin-derivative material layer.

The sensor devices of the present invention can be acoustic wave devices or optical transducers. Typically, acoustic wave devices are an arrangement of input and output interdigital transducers formed on a piezoelectric substrate such as quartz or lithium niobate. The input transducer, upon application of an alternating voltage, generates an alternating mechanical strain field because of the piezoelectric nature of the substrate. The alternating mechanical strain field launches an acoustic wave which if the wave travels along the substrate surface is called a surface acoustic wave (SAW) and if the wave travels through the bulk of the substrate is called an acoustic plate mode (APM). The acoustic wave interacts with a thin film formed on the device surface and is then reconverted into an electrical signal by the output transducer.

The velocity of the wave can be easily determined by operating the device as the feedback element of a oscillator circuit using an RF amplifier. Relative changes in frequency (f) can be directly related to relative changes in wave velocity (v). In situations where the velocity shift ($\Delta v$) is dominated by changes in the mass density of the film (m, mass/area), these frequency changes ($\Delta f$) can be directly related to changes in mass density by:

$$\Delta f/f_o = \Delta v/v_o = -c_m f_o m,$$

where $c_m$ is a mass sensitivity constant which depends on the piezoelectric substrate, and the subscript "o" indicates the unperturbed velocity or frequency.

Identification of species within a liquid or aqueous environment can be better achieved with an APM or Lamb wave device, which are each more effective in liquids than SAW devices which are highly attenuated by liquids contacting the device surface. Lamb waves propagate through materials of finite thickness. In contrast to a surface acoustic wave, which requires a propagation medium having a thickness on the order of tens to hundreds of times the wavelength of the surface acoustic wave propagating therethrough, Lamb waves require a propagation medium which is at most only several wavelengths in thickness.

Lamb wave sensors generally operate in a frequency range of from about 1 MHz to about 200 MHz, while SAW sensors generally operate in frequency range of from about 10 MHz to about 2,000 MHz. The lower-frequency operation of Lamb wave sensors can be more convenient in terms of costs for associated electronic equipment such as frequency counters and feedback amplifiers. Lamb devices are well known and are described, e.g., in U.S. Pat. Nos. 5,212,988, 5,189,914 and 5,129,262.

Figure 5:
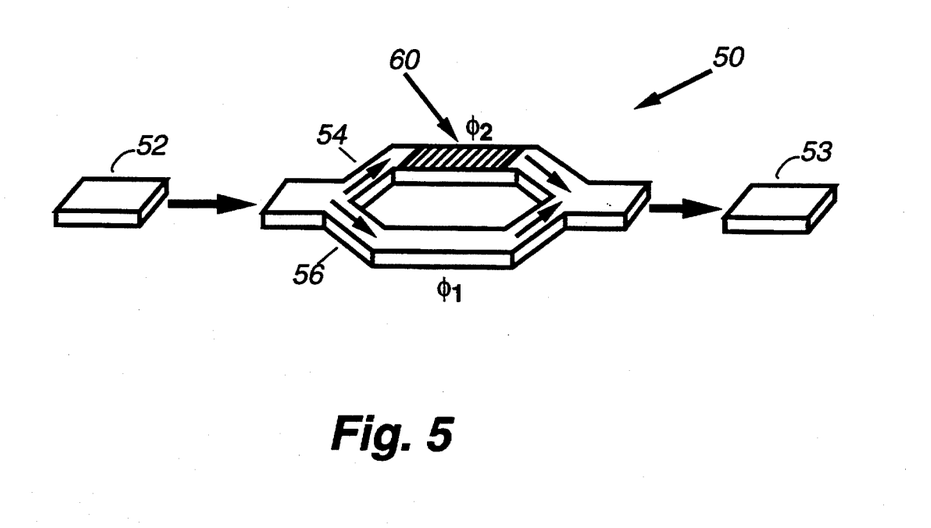
FIG. 5 illustrates an interferometer device in accordance with the present invention.

Suitable optical transducer devices can be, e.g., a Mach-Zehnder interferometer wherein the cyclodextrin-derivative is attached to an oxide surface of one arm of a split waveguide. After formation of any inclusion complexes, a refractive index change would result. The change in refractive index would be measured by a phase shift comparison between the light in the two arms of the interferometer, one arm coated with the selective film and one arm uncoated, thus allowing for determination and detection of selected chemical species. Generally, use of an optical transducer may allow for a more sensitive detection limit than by use of an acoustic wave device such as a SAW device or a Lamb wave device. Moreover, the response of SAW type devices and optical waveguide devices will generally be different for particular chemical species thereby providing complementary information about the identity of the chemical species. In FIG. 5, a Mach-Zehnder device 50 is shown with a light source 52 such as a diode laser which is split into two beams in arm 54 including a region of an optical surface coated with the selective cyclodextrin derivative coating and arm 56 including an uncoated optical surface region. The light is rejoined and passed into a detector 58 wherein any light intensity change as a result of a phase shift between the split beam can be attributed to formation of inclusion complexes between selected organic species and the cyclodextrin derivative material.

Figure 1:
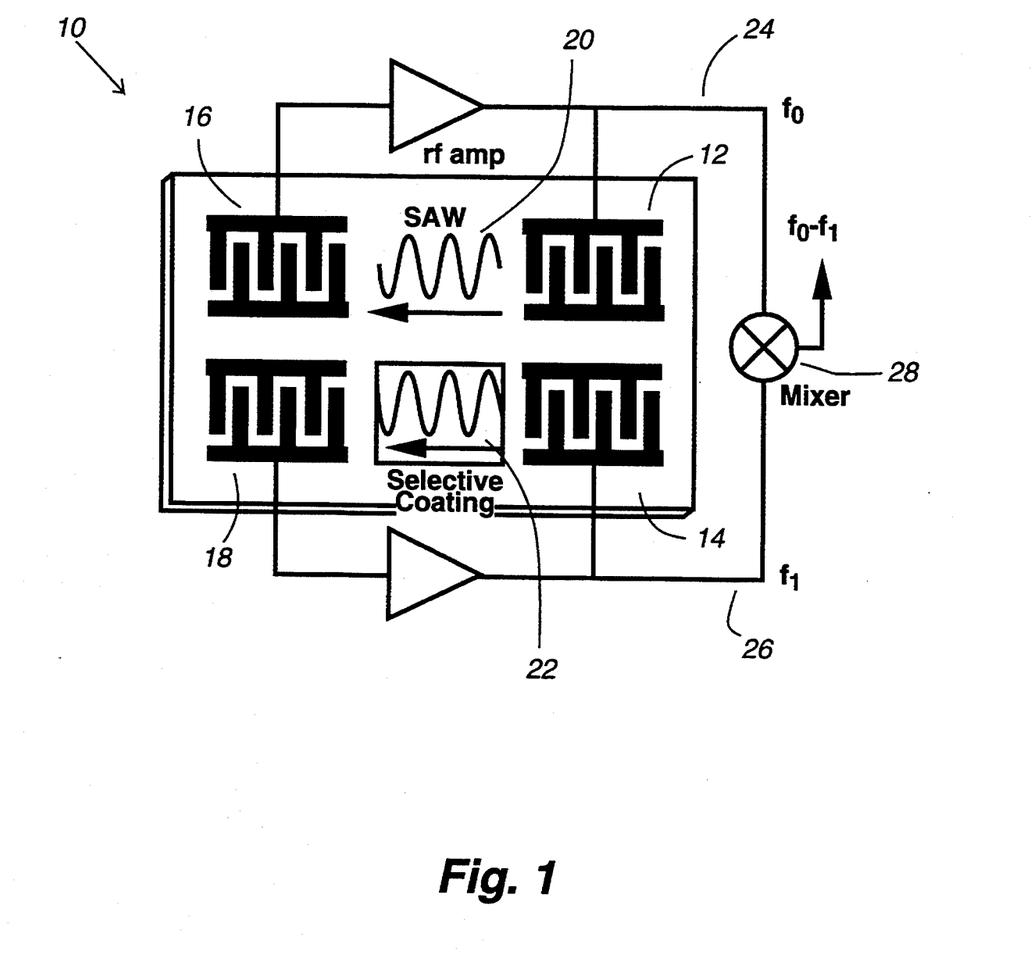
FIG. 1 is a schematic drawing of a SAW device including a coating in accordance with the present invention.

In FIG. 1, a SAW device 10 is shown including a pair of source transducers 12 and 14, a pair of pick up transducers 16 and 18, an uncoated region 20 between transducers 12 and 16, and a coated region 22 between transducers 14 and 18, said coating being a cyclodextrin-derivative coating. In operation, a surface acoustic wave is launched by applying a rf potential to the source transducers, e.g., source metal interdigital transducers. The wave transverses the surface of the piezoelectric quartz through the respective uncoated and coated regions and the wave is then converted back to an electical signal at the pick up transducers, e.g., pick up metal interdigital transducers. The respective electrical signals 24 and 26 are passed through a mixer 28 and a frequency shift is obtained. As the cyclodextrin coating changes in weight due to inclusion of, e.g., selected organic compounds, the frequency shift will change.

Figure 2:
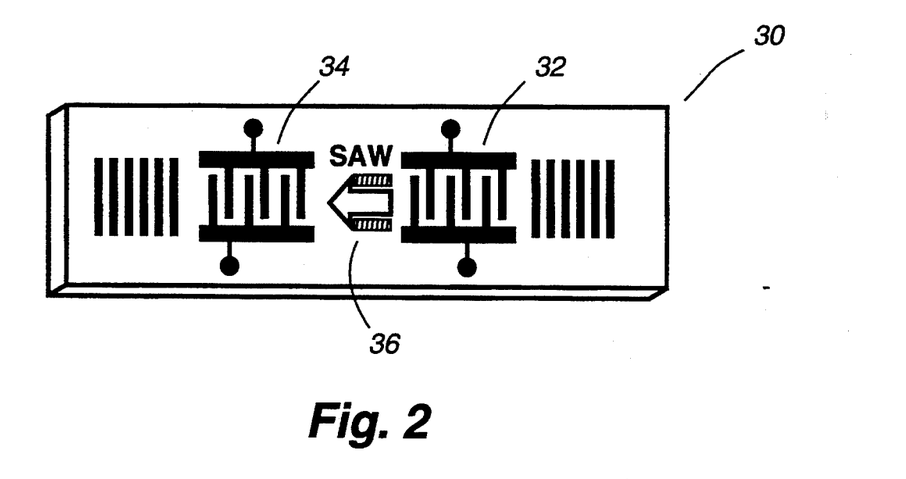
FIG. 2 is a schematic drawing of another type SAW device including a coating in accordance with the present invention.

In FIG. 2, a SAW resonator device 30 is shown including a source transducer 32, a pick up transducer 34, and a coated region 36 between transducers 32 and 34, said coating being a cyclodextrin derivative coating. Such a SAW resonator device sets up a resonating cavity in operation and such a SAW resonator device is available (without coating) from, e.g., MicroSensors Systems, Inc., as, e.g., an SAW-SR 200A (a 200 MHz on ST quartz). In operation, using both a coated and uncoated resonator device for comparison, a surface acoustic wave is launched by applying a rf potential to the source transducers of the respective resonators, e.g., source metal interdigital transducers. The wave transverses the surface of the piezoelectric quartz through the respective uncoated and coated resonators and the wave is then converted back to an electical signal at the pick up transducers, e.g., pick up metal interdigital transducers. The respective electrical signals are passed through a mixer and a frequency shift is obtained. As the cyclodextrin coating changes in weight due to inclusion of, e.g., selected organic compounds, the frequency shift will change.

Formation of a chemical separator in the present invention involves securing a cyclodextrin derivative material onto a suitable substrate, e.g., a quartz substrate, having a oxide surface to facilitate chemical bonding through, e.g., a silane linking agent. The resultant device can function as a chemical separator by forming the reverible inclusion complexes with selected materials such as organic compounds such as methanol and benzene. After initial formation of the inclusion complex, reversal can be accomplished, e.g., by varying the temperature up to about 60° C. thereby yielding a separation of the particular organic material from the chemical separator.

The present invention is more particularly described in the following examples which are intended as illustrative only, since numerous modifications and variations will be apparent to those skilled in the art.

All reagents were purchased from commercial sources except for cyclodextrin-derivatives. Examples A–D relate to the preparation of cyclodextrin derivatives. NMR spectra were obtained on a Brucker 250 MHz spectrometer.

EXAMPLE A

Preparation of α-Cyclodextrin-octadeca(2,3,6)benzoate was as follows. To a flask containing 4.865 gram of purified and dried α-cyclodextrin, a mixture of 120 mL of dry pyridine and 80 mL of benzoyl chloride was added. The solution turned yellow immediately, then red, and soon yielded a dark-brown solution. The resulting dark mixture was heated to 50° C. for 12 hours with stirring, and then pyridine was distilled off under vacuum at about 50° C. In a ice-water bath, 250 mL of anhydrous methanol was added slowly with a syringe while stirring the mixture to convert the remaining benzoyl chloride to methyl benzoate. Vacuum distillation of the mixture almost to dryness removed methanol and methyl benzoate. The resulting product was dissolved in 500 mL of anhydrous methanol. The product was precipitated out from the methanol solution by addition of 100 mL of deionized water followed by filtration to collect the crude product. The crude product was suspended in a methanol solution overnight for further extraction of any impurities. The final product was collected by filtration and then dried in vacuum. Analytical data was as follows. TLC (benzene/ethanol 4:1 v/v): Rf=0.9. FTIR (KBr): 1736 $cm^{-1}$ (vs, carbonyl); 1725 $cm^{-1}$ (vs, carbonyl); 1601 $cm^{-1}$ (w, phenyl); 1585 $cm^{-1}$ (m, phenyl); 1450 $cm^{-1}$ (phenyl). $^1H$ NMR ($CDCl_3$-d): δ4.26 (t, 6H-C(4), $J_{3,4}\approx J_{4,5}$=9.0 Hz); 4.83 (d×d, 6H-C(5), $J_{4,5}$=9.5 Hz, $J_{5,6a}$=4.0 Hz, $J_{5,6b}$<2.0 Hz); 4.87 (d×d, $6H_a$-C(6), $J_{gem}$=−12 Hz, $J_{5,6a}$=4.0 Hz); 5.00 (d×d, 6H-C(2), $J_{1,2}$=3.4 Hz, $J_{2,3}$=10.6 Hz); 5.06 (d, 6Hb-C(6), $J_{5,6b}$<2 Hz, $J_{gem}$=−12 Hz); 5.54 (d, 6H-C(1), $J_{1,2}$=3.4 Hz); 6.27 (d×d, 6H-C(3), $J_{2,3}$=10.4, $J_{3,4}$=9.0); 6.79 (t, 12H-Cm, $J_{o,m}\approx J_{m,p}$=7.7 HZ); 6.84 (t, 12H-$C_m$, $J_{o,m}\approx J_{m,p}$=7.7 HZ); 7.08 (d, 6H-$C_p$, $J_{m,p}$=7.7 HZ); 7.10 (d, 6H-$C_p$, $J_{m,p}$=7.7 HZ); 7.30 (d, 12H-$C_o$, $J_{o,m}$=7.5); 7.36 (d, 12H-$C_o$, $J_{o,m}$=7.5HZ); 7.46 (t, 12H-$C_m$, $J_{m,o}\approx J_{m,p}$=7.7 HZ); 7.52 (d, 6H-$C_p$, $J_{m,p}$=7.7 Hz); 8.15 (d, 12H-$C_o$, $J_{o,m}$=7.5).

EXAMPLE B

Preparation of α-Cyclodextrin-dodeca (2,3) benzoate was as follows. Under inert argon atmosphere, potassium (1.24 gram) was cut and weighed followed by transferring it into a flask. After removing the oil on the potassium metal with dry hexanes, 24.1 mL of anhydrous isopropanol was injected slowly with a syringe yielding a 1.32 Molar isopropoxide solution.

To a flask containing 5.1081 gram of a-cyclodextrin-octadeca(2,3,6)benzoate, 71.8 mL of dry benzene, 35.9 mL of anhydrous isopropanol, were added to dissolve the α-cyclodextrin-octadeca (2,3,6) benzoate. The resulting bright yellow solution was then cooled to 0° C. using a ice-water bath and 2.72 mL of 1.32 Molar isopropoxide were injected with a syringe. After stirring the solution for 12 hours, the alkaline solution was neutralized with 0.100 Molar aqueous HCl (~34.5 mL) in a 0° C. ice-water bath. Vacuum distillation was carried out to remove isopropanol and benzene. To the remaining aqueous mixture (~35 mL), 120 mL of chloroform was added. The organic layer was washed with deionized water for three times, dried over magnesium sulfate, and filtered. The crude product was precipitated out from chloroform solution by adding hexanes, filtered, and then dried in vacuum. The dried product was dissolved in about 20 mL of 4:1 (v/v) benzene/ethanol and loaded on a silica gel (silica gel 60, 0.040–0.063 mm) column (465 mm×41 mm). The first 320 mL of eluted solvent was discarded, then 20 mL of fractions were collected at a flow rate of −5.7 mL/min. The compounds in each fraction were monitored by TLC and the desired product was found in fractions 12–17. These fractions were combined and the solvent was evaporated under air flow. The resulting product was dissolved in a minimum amount of methanol with slight heating and double the volume of deionized water was added to the methanol solution to yield the white precipitate. The solid product was collected by filtration and dried in vacuum. Analytical data was as follows. TLC (benzene/ethanol 4:1 v/v): Rf=0.48. FTIR (KBr): 3426 cm$^{-1}$ (m, br, hydroxyl), 1736 cm$^{-1}$ (vs, carbonyl); 1726 cm$^{-1}$ (vs, sh, carbonyl); 1601 cm$^{-1}$ (w, phenyl); 1585 cm$^{-1}$ (w, phenyl); 1451 cm$^{-1}$ (m, phenyl), 1281 cm$^{-1}$ (s), 1176, 1096, 1044, 1027 cm$^{-1}$ (vs, br, C—O) 706 cm$^{-1}$ (vs, phenyl). $^1$H NMR (DMSO-d$_6$): 3.87 (br, d, 6H-C(5), J≈9); 4.17 (br, d, 6H-C(6), J≈9 Hz); 4.26 (d×d, 6H-C(4), J$_{3,4}$=9.0 Hz, J$_{4,5}$=9.5 Hz); 4.38 (br, d, 6H-C(6), J≈9 Hz); 4.88 (d×d, 6H-C(2), J$_{1,2}$=3.3 Hz, J$_{2,3}$=10.5 Hz); 4.92 (t, 6H-O-C(6), J≈4.5–5.9 Hz); 5.42 (d, 6H-C(1), J$_{1,2}$=3.2 Hz); 6.06 (d×d, 6H-C(3), J$_{3,4}$=9.0, J$_{2,3}$=10.5); 6.90 (t, 12H-C$_m$, J$_{o,m}$≈J$_{m,p}$=7.6–7.8 Hz); 7.05 (t, 12H-C$_m$, J$_{o,m}$≈J$_{m,p}$=7.7 Hz); 7.28 (t, 6H-C$_p$, J$_{m,p}$=7.6 Hz); 7.30 (d, 12H-C$_o$, J$_{o,m}$=7.8 Hz); 7.31 (t, 6H-C$_p$, J$_{m,p}$=7.6 Hz); 7.44 (d, 12H-C$_o$, J$_{o,m}$=7.8).

EXAMPLE C

β-Cyclodextrin-(2,3,6) perbenzoate was prepared as follows. To a flask containing 4.8703 gram of purified and dried β-cyclodextrin, a mixture of 140 mL of dry pyridine and 93 mL of benzoyl chloride was added. The solution appeared deep pink, and soon yielded a dark orange-brown solution. The resulting dark mixture was heated to 50° C. for 72 hours with stirring and the pyridine was distilled off under vacuum at about 50° C. In a ice-water bath, 250 mL of anhydrous methanol was added slowly with syringe while stirring the mixture to convert the remaining benzoyl chloride to methyl benzoate. Vacuum distillation was carried out to remove methanol and methyl benzoate until almost to dryness at 35° C. The resulting product was dissolved in 500 mL of anhydrous methanol. The product was precipitated out from the methanol solution by addition of 100 mL of deionized water followed by filtration to collect the crude product. The crude product was suspended in methanol solution overnight for further extraction of impurities. The final product was collected by filtration and then dried in vacuum. Analytical data was as follows. TLC (benzene/ethanol 1:5 v/v): R$_f$=0.68. FTIR (KBr): 1737 cm$^{-1}$ (vs, sh, carbonyl); 1729 cm$^{-1}$ (vs, carbonyl); 1602 cm$^{-1}$ (w, phenyl); 1584 cm$^{-1}$ (w, phenyl); 1451 cm$^{-1}$ (m, phenyl), 1276 cm$^{-1}$ (s), 1177, 1094, 1068, 1026 cm$^{-1}$ (vs, br, C—O) 706 cm$^{-1}$ (vs, phenyl). $^1$H NMR (CDCl$_3$-d): δ4.18 (s, br, 7H-C(4)); 4.69 (s, br, 7H-C(5)); 4.99 (s, br, 7H-C(6); 7H-C(2), 7H$_b$-C(6)); 5.59 (s, br, 7H-C(1)); 5.99 (s, br, 6H-C(3)); 6.95 (t, 28H-C$_m$, J$_{o,m}$≈J$_{m,p}$≈7.3–7.5 Hz); 7.19 (d, 14H-C$_p$, J$_{m,p}$≈6.8 Hz); 7.42 (d×d, 28H-C$_o$, J$_{o,m}$≈7.1–7.6); 7.53 (m, br, 14H-C$_m$, J$_{m,o}$≈J$_{m,p}$≈7.4 Hz; 6H-C$_p$); 8.15 (s, br, 14H-C$_o$).

EXAMPLE D

Preparation of β-Cyclodextrin-tetradeca(2,3)benzoate was as follows. Under inert argon atmosphere, potassium metal (2.82 gram) was cut and weighed followed by transferring it into a flask. After removing the oil on the potassium with dry hexanes, 54.8 mL of anhydrous isopropanol was injected slowly with syringe yielding a 1.32 Molar isopropoxide solution.

To a flask containing 4.9401 gram of β-cyclodextrin-octadeca(2,3,6)benzoate, 69.4 mL of dry benzene and 34.7 mL of anhydrous isopropanol were added to dissolve the β-cyclodextrin-octadeca(2,3,6)benzoate. The resulting bright yellow solution was then cooled to 0° C. using a ice-water bath and 2.25 mL of 1.32 Molar isopropoxide were injected with a syringe. After stirring the solution for 12 hours, the alkaline solution was neutralized with 0.100 Molar aqueous HCl (~28.5 mL) in a 0° C. ice-water bath. Vacuum distillation was carried out to remove isopropanol and benzene. To the remaining aqueous mixture, 20–30 mL of chloroform was added. The organic layer was washed three times with deionized water, dried over magnesium sulfate, and filtered. The final white product was precipitated out from chloroform solution by adding hexanes, filtered, and then dried in vacuum. Analytical data was as follows. TLC (methanol 4:1 v/v): R$_f$=0.85. FTIR (KBr): 3421 cm$^{-1}$ (m, br, hydroxyl), 3064 cm$^{-1}$ (w, Ar-H), 2934 cm$^{-1}$ (w, C-H), 1736 cm$^{-1}$ (vs, sh, carbonyl); 1727 cm$^{-1}$ (vs, carbonyl); 1602 cm$^{-1}$ (w, phenyl); 1584 cm$^{-1}$ (w, phenyl); 1451 cm$^{-1}$ (m, phenyl), 1276 cm$^{-1}$ (s), 1176, 1096, 1047, 1026 cm$^{-1}$ (vs, br, C—O) 706 cm$^{-1}$ (vs, phenyl).

EXAMPLE 1

The fused quartz substrates were ultrasonically cleaned in a 10% by weight detergent solution for 10 min and then refluxed in an aqueous 1% by weight tetra-sodium ethylenediamine tetraacetate (EDTA) solution for 10 minutes, followed by another 10 minute sonication at ambient temperature. Finally, the substrates were thoroughly rinsed with deionized water, rinsed with acetone and then sputter cleaned using an argon plasma at 10$^{-3}$ torr for more than 30 minutes. Polished Si wafers were cleaned by sonicating in a 10% by weight detergent solution for 10 minutes and then sputter cleaned using an argon plasma for 30 minutes. Surface acoustic resonators were cleaned by washing in a 10% by weight detergent solution for 10 minutes and then sputter cleaned using an argon plasma for 30 minutes. All substrates were used immediately after cleaning.

EXAMPLE 2

A silane coupling layer was formed on the substate surfaces as follows. Cleaned substrates were sealed in a dry chamber which was connected with Teflon 1/16″ tubing to a upstream safety trap followed by a silane container and then another safety trap. The safety traps on either upstream or downstream of the silane container prevent accidental carry-over of silane into the system. Pressurized argon gas was regulated to ~20 psi and fed into a flow controller before entering the system. The argon flows through the first safety trap, bubbles through silane, and exits into the second safety trap before entering the final substrate chamber. The desired substrates were exposed to the vapor of 1,6-bis(trichlorosilyl)hexane by bubbling argon through this system at 450 mL/minute for 16 hours at room temperature.

EXAMPLE 3

The addition of a cyclodextrin derivative layer ($\alpha$-Cyclodextrin-dodeca(2,3)benzoate from example B) to the silane coupling layer was as follows. To a substrate with the newly formed 1,6-bis(trichlorosilyl)hexane layer in the sealed container, 10 mL of 5.0 millimolar (mM) $\alpha$-Cyclodextrin-dodeca(2,3)benzoate in dry benzene solution was injected with a syringe. The substrates were then immersed in the clear solution for about 2 hours at room temperature. The cyclodextrin deivative coated substrates were transferred into a benzene solvent and cleaned four times using two-minute sonications. After cleaning, the substrates were thoroughly rinsed with acetone and then dried under the flow of air.

The following data characterize the formation of cyclodextrin layer. p-Polarized variable-angle internal attenuated total-reflection infrared spectroscopy (Ge internal reflection element, 45° incident angle, monolayer of $\alpha$-cyclodextrin derivative on Si wafer): $v_a=2926$ cm$^{-1}$ (CH$_2$ in coupling layer); $v_s=2855$ cm$^{-1}$ (CH$_2$ in coupling layer); $v(C=O)=1740$, 1734 cm$^{-1}$; $v$(phenyl)=1452, 1284 cm$^{-1}$; $v(C-O)=1130$, 1070, 1029 cm$^{-1}$; $v$(phenyl)=706. s-Polarized variable-angle internal attenuated total-reflection infrared spectroscopy (Ge internal reflection element, 45° incident angle, monolayer of $\alpha$-cyclodextrin derivative on Si wafer): $v_a=2926$ cm$^{-1}$ (CH$_2$ in coupling layer); $v_s=2855$ cm$^{-1}$ (CH$_2$ in coupling layer); $v(C=O)=1740$, 1734 cm$^{-1}$. Surface coverage by SAW mass transduction: $3.27 \times 10^{-7}$ g/cm$^{-2}$.

EXAMPLE 4

The addition of a $\beta$-Cyclodextrin-tetradeca(2,3)benzoate layer to a substrate with the silane coupling layer as in example 2 was as follows. To substrates with the newly formed 1,6-bis(trichlorosilyl)hexane layer, 10 mL of 1.0 mM $\beta$-Cyclodextrin-dodeca(2,3)benzoate in dry acetonitrile solution was injected with a syringe. The substrates were then immersed in the clear solution for about 12 hours at room temperature. The cyclodextrin derivative coated substrates were transferred into a acetonitrile solvent and cleaned four times using two-minute sonications. After cleaning, the substrates were thoroughly rinsed with acetone and then dried under the flow of air.

The following data characterize the formation of cyclodextrin derivative layer. p-Polarized variable-angle internal attenuated total-reflection infrared spectroscopy (Ge internal reflection element, 45° incident angle, monolayer of $\beta$-cyclodextrin derivative on Si wafer): $v_a=2929$ cm$^{-1}$ (CH$_2$ in coupling layer); $v_s=2858$ cm$^{-1}$ (CH$_2$ in coupling layer); $v_{C=O}=1739$-1730 cm$^{-1}$ (carbonyls).

EXAMPLE 5

Figure 3:
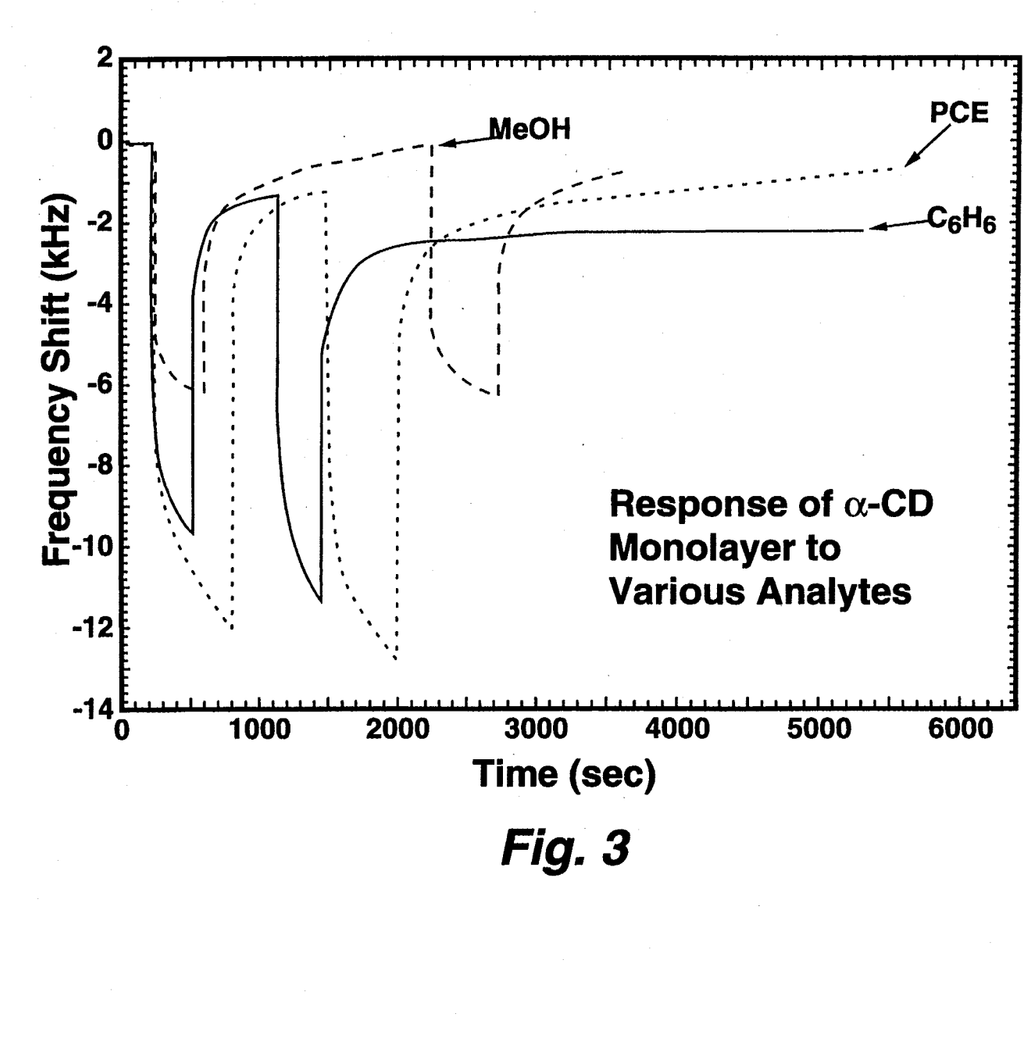
FIG. 3 illustrates the response of a 200 MHz SAW resonator microsensor coated with a cyclodextrin derivative in accordance with the present invention to selected organic compounds.

A SAW resonator including one substrate coated with the cyclodextrin derivative as in example 3 was exposed to various target gaseous organic compounds by passing at room temperature dry nitrogen saturated with the respective target organic compound at a flow rate of 0.12 liters per minute (L/min) and a partial pressure of the organic compound calibrated gravimetrically using a liquid nitrogen trap. Upon exposure to the various organic compounds the cyclodextrin derivative coated SAW resonator responded both quickly (a matter of seconds) and reversibly as shown in FIG. 3.

The results demonstrate that a chemical sensor including an active responsive material of a cyclodextrin derivative can detect the presence of volatile organic species in a real time situation and that such the active responsive material of such a sensor operates reversibly.

Although the present invention has been described with reference to specific details, it is not intended that such details should be regarded as limitations upon the scope of the invention, except as and to the extent that they are included in the accompanying claims.

What is claimed is:

1. An article of manufacture comprising a substrate including an oxide surface layer and a selective thin film of a cyclodextrin derivative chemically bound upon said substrate, said film is capable of inclusion of a selected organic compound therewith.

2. The article of claim 1 wherein said article is a chemical sensor and said sensor is capable of detecting a resultant mass change from inclusion of the selected organic compound.

3. The article of claim 1 wherein said article is a chemical sensor and said sensor is capable of detecting a resultant reflective index change from inclusion of the selected organic compound.

4. The sensor of claim 2 wherein said selective thin film of a cyclodextrin derivative is chemically bound upon said substrate by a silane linking agent.

5. The sensor of claim 4 wherein said selective thin film includes multiple layers of a cyclodextrin derivative.

6. The sensor of claim 4 wherein the silane linking agent is 1,6-Bis(trichlorosilyl)hexane.

7. The sensor of claim 2 wherein said substrate is a piezoelectric substrate.

8. The article of claim 1 wherein said article is a separator and said separator is capable of reversibly selectively separating a selected organic compound.

9. The article of claim 8 wherein said substrate comprises glass beads.

10. The article of claim 5 wherein different layers of the cyclodextrin derivative include different chemical functional groups.

11. The article of claim 5 wherein the cyclodextrin derivative includes chemical functional groups.

12. The article of claim 5 wherein a second layer of cyclodextrin derivative is a spin-cast deposited layer upon an initial self assembled cyclodextrin derivative layer.

* * * * *